(12) United States Patent
Behnk

(10) Patent No.: US 7,964,145 B2
(45) Date of Patent: Jun. 21, 2011

(54) AGGREGOMETER

(76) Inventor: Holger Behnk, Hamburg (DE)

( * ) Notice: Subject to any disclaimer, the term of this patent is extended or adjusted under 35 U.S.C. 154(b) by 171 days.

(21) Appl. No.: 12/386,532

(22) Filed: Apr. 20, 2009

(65) Prior Publication Data

US 2009/0261803 A1 Oct. 22, 2009

(30) Foreign Application Priority Data

Apr. 22, 2008 (EP) ..................................... 08007779

(51) Int. Cl.
*G01N 27/00* (2006.01)
(52) U.S. Cl. .............................. 422/73; 436/69; 324/71.1
(58) Field of Classification Search .................... 422/72; 436/69; 324/71.1
See application file for complete search history.

(56) References Cited

U.S. PATENT DOCUMENTS

| 3,486,859 A | 12/1969 | Greiner et al. |
| 4,725,554 A * | 2/1988 | Schildknecht .................. 436/69 |
| 5,491,408 A | 2/1996 | Rousseau |
| 7,021,122 B1 | 4/2006 | Rosemberg et al. |

FOREIGN PATENT DOCUMENTS

| DE | 698 21 364 T2 | 10/2004 |
| WO | WO2005059532 A1 | 6/2005 |

* cited by examiner

*Primary Examiner* — In Suk Bullock
*Assistant Examiner* — Timothy G Kingan
(74) *Attorney, Agent, or Firm* — Alix, Yale & Ristas, LLP

(57) ABSTRACT

An aggregometer for measuring and recording platelet aggregation with at least one measurement cuvette having two electrodes, with a device for moving the liquid to be examined and with measurement and evaluation electronics connected to the electrodes via contact elements, is characterized in that the measurement cuvette comprises two adjacently arranged, upwardly open partial spaces which are only connected to one another in the lower region, in that the electrodes are designed as metal spheres inserted in the bottom of the measurement cuvette and in that the device for moving the liquid is a pumping device which can be placed on one of the partial spaces in a substantially sealing manner and which periodically and alternately generates low and excess pressure.

20 Claims, 3 Drawing Sheets

AGGREGOMETER

BACKGROUND

The disclosure relates to an aggregometer for measuring and recording platelet aggregation with at least one measurement cuvette having two electrodes, with a device for moving the liquid to be examined and with measurement and evaluation electronics connected to the electrodes via contact elements.

A known aggregometer of this type (DE 698 21 364 T2) is used to measure and record platelet aggregation. In its protein-rich fluid (the plasma), blood has three main groups of cells, specifically: red blood cells, white blood cells and platelets. Platelets can be exposed to an aggregation-adhesion reaction if they come into contact with particular materials and chemicals. In this case, they change their shape and become approximately spherical. In the process, they develop long appendages and as a result of this they become adhesive. The platelets then adhere to one another and to damaged tissue.

This aggregation is very important, for example, in the case of operations. Aggregation can be reduced by certain medications, but it is necessary to know whether a certain medication dose actually reduces the aggregation, since different people react differently to the medication.

In a known method, the aggregation reaction in samples of platelet-rich plasma is analysed by measuring the transparency of the sample. However, to this end it is necessary to separate the blood in a complex manner by centrifugation, as a result of which the properties of the platelets can be falsified.

In the mentioned prior art, this disadvantage is avoided by mixing the blood which covers two electrodes. If platelets are deposited on the electrodes, the electrical resistance measured will increase and so the aggregation can be determined in this manner. In contrast to other methods, the measurement can also be conducted using blood; centrifugation is not necessary.

Disadvantages of this known aggregometer are, firstly, that the electrodes are ductile and so the electrical characteristics are not constant in the measurement. The stirring rod used to move the blood will locally move the blood vigorously in its vicinity, whereas regions which are situated further away from the stirring rod will be moved less. Both do not correspond to physiological processes in human or animal bodies.

Hence, an aggregometer is provided in which the measurement can be carried out in blood that moves more evenly, without the electrical properties of the electrodes varying.

SUMMARY

A measurement cuvette comprises two adjacently arranged, upwardly open partial spaces which are only connected to one another in the lower region. The electrodes are designed as metal spheres inserted in the bottom of the measurement cuvette. The device for moving the liquid is a pumping device which can be placed on one of the partial spaces in a substantially sealing manner and which periodically and alternately generates low and excess pressure.

The measurement cuvette comprises two adjacently arranged, upwardly open partial spaces. Said partial spaces are connected to one another in the lower region. In this case, the electrodes are designed as metal spheres which are inserted in the bottom of the measurement cuvette and have a constant spacing and unchangeable surfaces such that the electrical properties in the measurements are always constant and the same. A pumping device is then placed onto one of the partial spaces in a substantially sealing manner and said pumping device periodically and alternately generates slightly lower and slightly excess pressure in this partial space. As a result of this, the liquid (e.g. the blood) is moved to and fro from one partial space and into the other partial space and in each case passes over the spheres. This movement, which represents a steady blood flow, in this case also substantially corresponds to the flow properties of the blood in the human and animal body.

Expediently, the metal spheres are moulded or pressed into the bottom of the cuvette. Expediently, they are made of a noncorrosive material, in particular stainless steel. On the other hand, the metal spheres can however also be coated by a noncorrosive material, in particular a noble metal such as gold.

In another advantageous embodiment, the metal spheres are coated with a reagent.

If the pumping velocity can be changed, different flow velocities can be attained.

Expediently, the pump has a cylinder and a piston which can be moved to and fro by an eccentric drive. By changing the velocity of the eccentric drive it is possible to change the pumping frequency or pumping velocity.

Expediently, the partial space onto which the pumping device can be placed has substantially parallel walls. The other partial space however expediently expands upwards like a funnel in order to simplify the insertion of the blood sample.

Expediently, the contact elements, by means of which the metal spheres are connected to the measurement electronics, are designed to be resilient. This facilitates interchanging different cuvettes or the insertion into a measurement station.

This is particularly advantageous if a plurality of measurement cuvettes are arranged next to one another. In this case, provision can be made for devices so that the individual cuvettes can simultaneously be connected to the measurement and evaluation electronics by the metal spheres being connected to the electronics with the aid of their contact elements and with one or more pumping devices being placed on the measurement cuvettes and being operated.

The measurement cuvettes can be produced as single-use parts. It is particularly expedient if they are injection-moulded parts from blood-compatible plastic materials selected from polystyrene, poly(methyl methacrylate), polyethylene and similar plastics.

DETAILED DESCRIPTION

Figure 1:
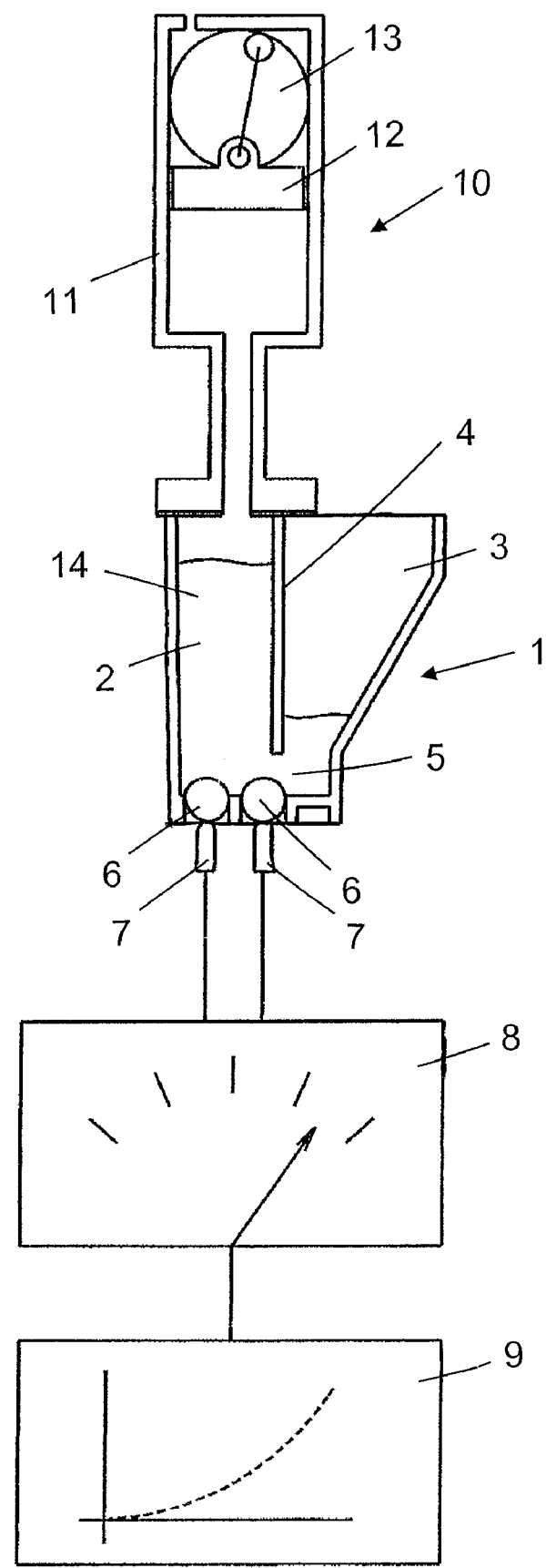
FIG. 1 schematically shows the design of an aggregometer in a first phase of operation.

As illustrated in FIG. 1, the measurement cuvette 1 has two partial spaces 2 and 3. In this case, the partial space 2 has substantially parallel walls, while the partial space 3 expands upwards like a funnel. The two partial spaces 2 and 3 are separated by an intermediate wall 4 which only leaves open a passage 5 in the lower region. Here, provision is made for two metal spheres 6 which in particular are moulded or pressed into the bottom and connected, via resilient contact elements 7, to the measurement electronics 8, with it being possible to graphically display, on 9 for example, the measurement results thereof.

Figure 2:
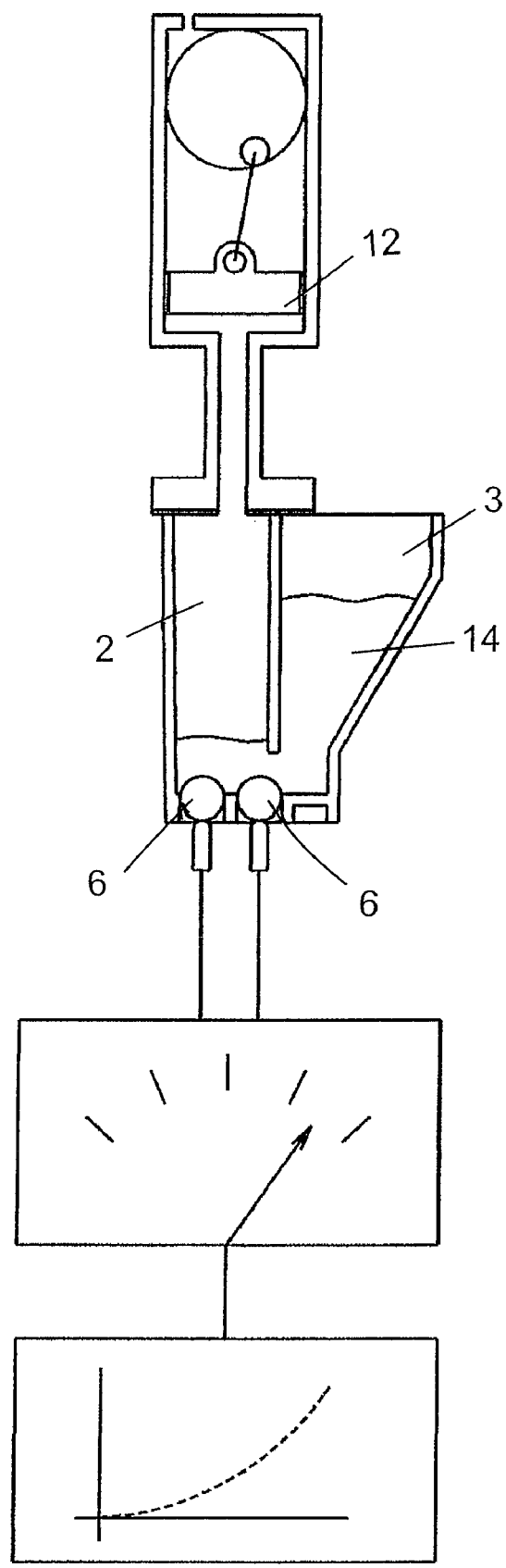
FIG. 2 shows the design of the aggregometer in a second phase of operation.

A pumping device 10, which has a cylinder 11 with a piston 12 that can be moved up and down using an eccentric drive 13, is placed on the first partial space 2 of the measurement cuvette 1 in a substantially sealing manner. In the operating state illustrated in FIG. 1, the piston 12 is located at the top and thus draws the blood 14 into the first partial space 2. In the operating state illustrated in FIG. 2, the piston 12 is located at the bottom and thus presses the blood 14 into the second partial space 3. During this to and fro motion, the blood 14 passes over the metal spheres 6.

If aggregation of platelets occurs, there is an increase in the electrical resistance measured between these two electrodes 6. It is therefore possible to measure the aggregation behaviour of the blood, in particular as a function of the dispensed medication as well. This makes it possible, for example, to determine whether specific medication (e.g. acetylsalicylic acid) is effective and how it works.

Figure 3:
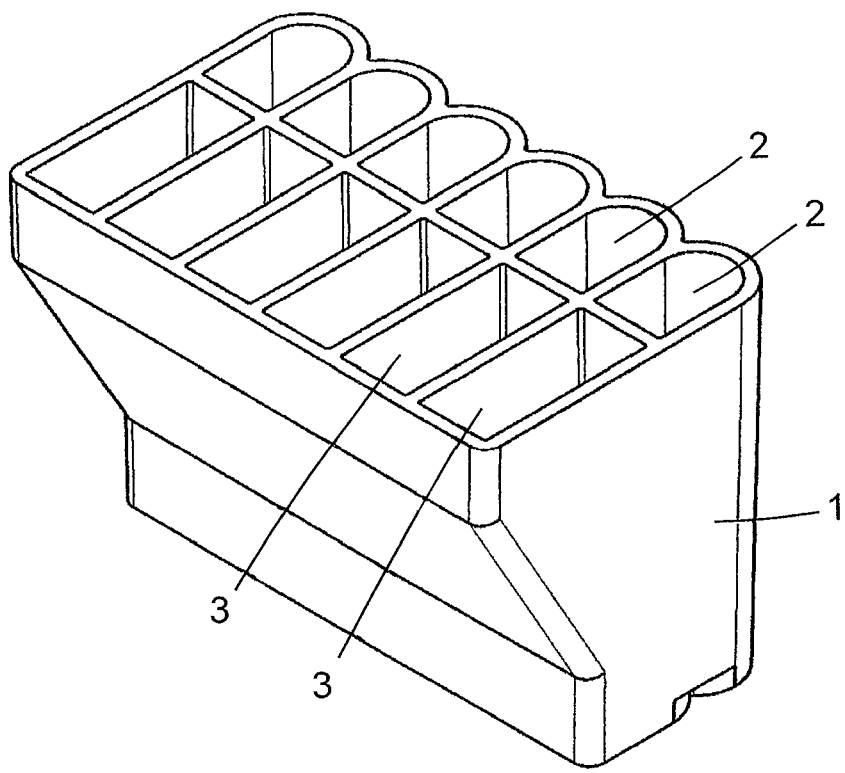
FIG. 3 shows another embodiment of the measurement cuvettes in a perspective view.
Figure 4:
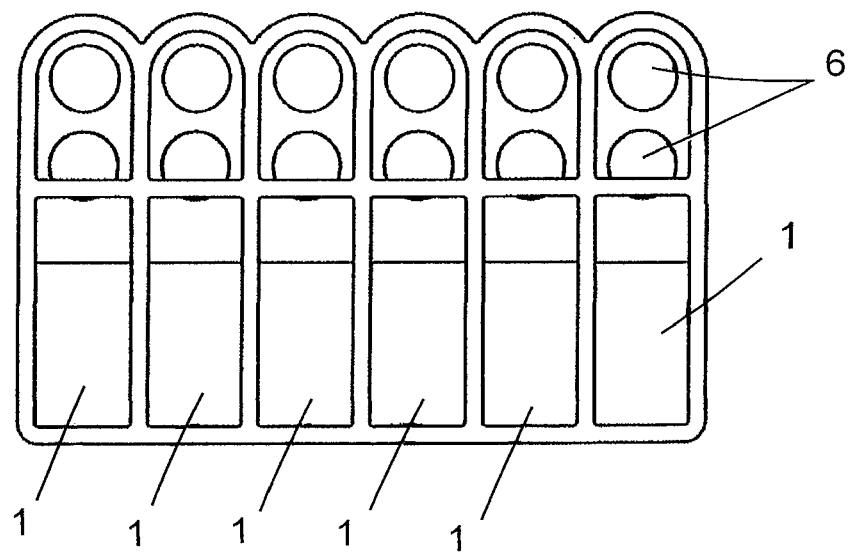
FIG. 4 shows the measurement cuvettes in accordance with FIG. 3 in a plan view from above.

Here, the measurement can be carried out both in the laboratory and the operating theatre. It can also be automated. This is the case in particular when an apparatus in accordance with FIG. 3 is used, where a plurality of cuvettes 1 are arranged adjacently. The individual cuvettes 1 can then simultaneously be connected to the measurement electronics 8 using the resilient contacts 7. Once the pumping device 10 or plurality of pumping devices is/are placed onto the cuvettes, the measurement can be carried out simultaneously for all cuvettes.

The invention claimed is:

1. An aggregometer for measuring and recording platelet aggregation with at least one measurement cuvette having a bottom and two electrodes, with a device for moving the liquid to be examined and with measurement and evaluation electronics connected to the electrodes via contact elements, characterized in that the measurement cuvette comprises two adjacently arranged, upwardly open partial spaces which are only connected to one another in a lower region, in that the electrodes are designed as metal spheres inserted in the bottom of the measurement cuvette and in that the device for moving the liquid is a pumping device which can be placed on one of the partial spaces in a substantially sealing manner and which periodically and alternately generates low and excess pressure.

2. The aggregometer according to claim 1, characterized in that the metal spheres are moulded or pressed into the bottom of the cuvette.

3. The aggregometer according to claim 1, characterized in that the metal spheres are made of stainless steel.

4. The aggregometer according to claim 1, characterized in that the metal spheres are coated.

5. The aggregometer according to claim 4, characterized in that the metal spheres are coated with a material selected from the group consisting of silver, a noncorrosive material, a noble metal and a reagent.

6. The aggregometer according to claim 1, characterized in that the pumping velocity can be changed.

7. The aggregometer according to claim 1, characterized in that the pumping device has a cylinder and a piston which can be moved to and fro by an eccentric drive.

8. The aggregometer according to claim 1, characterized in that the pumping device is a diaphragm pump.

9. The aggregometer according to claim 1, characterized in that the partial space onto which the pumping device can be placed has substantially parallel walls while the other partial space expands upwards like a funnel.

10. The aggregometer according to claim 1, characterized in that the contact elements are resilient.

11. The aggregometer according to claim 1, characterized in that a plurality of measurement cuvettes are arranged next to one another.

12. The aggregometer according to claim 11, characterized in that the individual cuvettes can simultaneously be connected to the measurement and evaluation electronics by the metal spheres being connected to the electronics with the aid of their contact elements, with one or more pumping devices being placed on the measurement cuvettes and being operated.

13. The aggregometer according to claim 1, characterized in that the cuvettes are injection-moulded parts from blood-compatible plastic materials selected from the group consisting of polystyrene, poly(methyl methacrylate) and polyethylene.

14. The aggregometer according to claim 2, characterized in that the metal spheres are made of stainless steel.

15. The aggregometer according to claim 2, characterized in that the metal spheres are coated.

16. The aggregometer according to claim 3, characterized in that the metal spheres are coated.

17. The aggregometer according to claim 14, characterized in that the metal spheres are coated.

18. The aggregometer according to claim 2, characterized in that the pumping velocity can be changed.

19. The aggregometer according to claim 3, characterized in that the pumping velocity can be changed.

20. The aggregometer according to claim 4, characterized in that the pumping velocity can be changed.

* * * * *